United States Patent
Parish et al.

(10) Patent No.: US 6,271,215 B1
(45) Date of Patent: Aug. 7, 2001

(54) SULFATED OLIGOSACCHARIDES HAVING ANTICOAGULANT/ANTITHROMBOTIC ACTIVITY

(75) Inventors: Christopher Richard Parish; William Butler Cowden, both of Campbell (AU)

(73) Assignee: The Australian National University (AU)

( * ) Notice: Subject to any disclaimer, the term of this patent is extended or adjusted under 35 U.S.C. 154(b) by 0 days.

(21) Appl. No.: 09/380,899

(22) PCT Filed: Mar. 10, 1998

(86) PCT No.: PCT/AU98/00151
§ 371 Date: Nov. 15, 1999
§ 102(e) Date: Nov. 15, 1999

(87) PCT Pub. No.: WO98/40081
PCT Pub. Date: Sep. 17, 1998

(30) Foreign Application Priority Data

Mar. 11, 1997 (AU) .................................. PO 5562

(51) Int. Cl.⁷ .................................. A61K 31/715
(52) U.S. Cl. ............................................. 514/54
(58) Field of Search ................ 424/180; 514/54, 514/2, 24, 25, 63; 523/41.1, 59, 109, 118

(56) References Cited

U.S. PATENT DOCUMENTS

| | | | | |
|---|---|---|---|---|
| 4,402,946 | * | 9/1983 | Thompson | 424/180 |
| 4,496,550 | | 1/1985 | Kabivitrum . | |
| 4,826,827 | * | 5/1989 | Lormeau et al. | 514/56 |

FOREIGN PATENT DOCUMENTS

| | | |
|---|---|---|
| 70519/81 | 11/1981 | (AU) . |
| 42637/85 | 11/1985 | (AU) . |
| 77425/91 | 10/1991 | (AU) . |
| 84714/91 | 4/1992 | (AU) . |
| 12127/92 | 9/1992 | (AU) . |
| 19025/92 | 10/1992 | (AU) . |
| 68448/94 | 12/1994 | (AU) . |
| 38879/95 | 4/1996 | (AU) . |
| 80136/94 | 4/1996 | (AU) . |
| 53933/96 | 10/1996 | (AU) . |
| WO 96/33726 | * 10/1996 | (AU) . |
| 2254083 | 9/1992 | (GB) . |

OTHER PUBLICATIONS

Biochemistry vol. 31 No. 8, Mar. 1992, Horne A et al "1H NMR Spectroscopic Studies on the Interactions between Human Plasma Antithrombin III and Defined Low Molecular Weight Heparin Fragments" pp. 2286–2294.

European Journal of Biochemistry vol. 176 No. 3, 1988, Petitou M. et al. "Interaction of Heparin and Antithrombin III: The Role of O–sulfate Groups" pp. 637–640 see Abstract, p. 637 first paragraph to last paragraph, Figure 1 p. 638.

Glycobiology vol. 3 No. 6, Dec. 1993 Hahnenberger R. et al. "Low–Suphated Oligosaccharides derived from Heparin Suphate inhibit Normal Angiogensis" p. 567–573 see pp. 567 paragraph 3, Figure 1 p. 568.

* cited by examiner

Primary Examiner—Jose' G. Dees
Assistant Examiner—Konata M. George
(74) Attorney, Agent, or Firm—Fulwider Patton Lee & Utecht, LLP

(57) ABSTRACT

A method for the anticoagulant and/or antithrombotic treatment of a human or other warm-blooded animal patient in need of such treatment, comprises administration to the patient of an effective amount of at least one sulfated oligosaccharide, wherein the oligosaccharide has the general formula I:

$$R_1-(R_x)_n-R_2 \qquad (I)$$

wherein $R_1$ and $R_2$ and each $R_x$ represents a monosaccharide unit, all of which may be the same or different, adjacent monosaccharide units being linked by $1\to2$, $1\to3$, $1\to4$ and/or $1\to6$ glycosidic bonds and n is an integer of from 1 to 6.

19 Claims, 3 Drawing Sheets

SULFATED OLIGOSACCHARIDES HAVING ANTICOAGULANT/ANTITHROMBOTIC ACTIVITY

FIELD OF THE INVENTION

This invention relates to sulfated oligosaccharides, and in particular to the use of certain sulfated oligosaccharides as anticoagulant and/or antithrombotic agents.

BACKGROUND TO THE INVENTION

Heparin, a sulfated glycosaminoglycan produced by mammalian mast cells, has been used extensively during the last 50 years as an anticoagulant for the prevention of post-operative thrombosis and the treatment of acute venous thrombosis. Heparin predominantly exerts its anticoagulant activity by accelerating the ability of the protease inhibitor antithrombin III to inactivate a number of key proteases in the coagulation cascade (1, 2), most notably factor Xa and thrombin, thrombin being the terminal enzyme in the cascade which converts soluble fibrinogen to insoluble fibrin. In fact, a specific pentasaccharide has been identified in heparin which binds with high affinity to antithrombin III and produces a conformational change in the inhibitor (3). This pentasaccharide is sufficient to enhance inactivation of proteases, such as factor Xa, by antithrombin III. In contrast, heparin needs to crosslink antithrombin III with thrombin for enhanced thrombin inactivation to occur (3).

Despite its widespread clinical use as an anticoagulant, however, heparin suffers from a number of major disadvantages. First, it is structurally extremely diverse, varying in its molecular weight, monosaccharide sequence and sulfation pattern (4). As a result of this diversity, less than 50% of heparin molecules in most preparations actually contain the antithrombin III binding pentasaccharide (1–3). Thus, the quality control of different heparin batches is difficult. Second, heparin is an animal byproduct and consequently suffers from the risk of contamination with animal pathogens, a major concern for present day regulatory agencies. Third, heparin can only be administered intravenously as, due to its high molecular weight, it exhibits poor bioavailability when injected subcutaneously (5, 6). Also, the high molecular weight of heparin (10–15kDa) precludes effective oral delivery of the drug. Fourth, in terms of clinical efficacy, heparin exhibits an extremely steep dose response curve. Thus, the coagulation time of patient's plasma must be continually monitored to ensure that drug overdose does not occur. Administration of appropriate heparin doses is further confounded by significant patient variability in heparin responsiveness. These difficulties lead to unacceptable bleeding being a complication of heparin therapy, particularly when the drug is being used as a long term treatment (5, 6). Finally, a significant number of patients develop heparin-induced thrombocytopenia (HIT) following prolonged heparin exposure (5, 6), a condition which precludes future heparin use in these individuals.

In an attempt to overcome some of the problems associated with heparin, a number of low molecular weight (LMW) (mol. wt. 4000–6500) heparin preparations have been developed and licenced (5, 6). These preparations have retained the anti-factor Xa and anti-thrombotic activities of native heparin but are less potent anticoagulants. As a result, the LMW heparins are less likely to induce bleeding complications in patients. Furthermore, due to their smaller size, they have improved bioavailability and can be administered subcutaneously.

An alternative approach has been to use the related glycosaminoglycan, dermatan sulfate, as an antithrombotic agent (7). Interestingly dernatan sulfate, unlike heparin, catalyses thrombin inhibition by a second natural inhibitor of thrombin, heparin cofactor II (8). However, despite the availability of LMW heparins and dermatan sulfate, there is still a considerable need for structurally well-defined anticoagulants and/or antithrombotics which are not animal derived, give reproducible patient responses, can be orally administered and are not prone to inducing thrombocytopenia.

Prior International Patent Application No. PCT/AU96/00238 discloses the preparation of a class of sulfated oligosaccharides based on polymers of monosaccharide units linked by 1→2, 1→3, 1→4 and/or 1→6 glycosidic bonds and consisting of from 3 to 8 monosaccharide units, and the use of these sulfated oligosaccharides as potent inhibitors of human angiogenesis, tumour metastasis and inflammation.

In work leading to the present invention, it has been shown that these sulfated oligosaccharides may be used as anticoagulant/antithrombotic agents to overcome the many problems associated with glycosaminoglycan-derived anticoagulants/antithrombotics. In particular, it has been shown that the sulfated penta- or hexa-saccharides possess a well defined structure, a broad therapeutic window, a highly reproducible patient response, a probably reduced chance of inducing HIT-like syndromes and the potential for oral delivery. Furthermore, these sulfated oligosaccharides do not act via antithrombin III but appear to inhibit coagulation by activating heparin cofactor II. Thus, the active sulfated oligosaccharides to some extent resemble the sulfated polysaccharide dermatan sulfate, rather than heparin, in their mode of action. Such oligosaccharides may be used for both prophylaxis and treatment of many thrombotic and cardiovascular diseases, the most notable of these being deep venous thrombosis, pulmonary embolism, thrombotic stroke, peripheral arterial thrombosis, unstable angina and myocardial infarction. Furthermore, effective oral delivery of the sulfated oligosaccharides makes these agents an alternative to warfarin, a widely used oral anticoagulant with severe side effects.

SUMMARY OF THE INVENTION

In accordance with one aspect, the present invention provides a method for the anticoagulant and/or antithrombotic treatment of a human or other warm blooded animal patient in need of such treatment, which comprises administration to the patient of an effective amount of at least one sulfated oligosaccharide, wherein the oligosaccharide has the general formula I:

$$R_1-(R_x)_n-R_2 \qquad (I)$$

wherein $R_1$ and $R_2$ and each $R_x$ represents a monosaccharide unit, all of which may be the same or different, adjacent monosaccharide units being linked by 1→2, 1→3, 1→4 and/or 1→6 glycosidic bonds; and n is an integer of from 1 to 6, preferably 3 or 4.

Preferably, the sulfated oligosaccharides have the general formula II:

$$R-(R)_n-R \qquad (II)$$

wherein each R group represents the same and each represents a monosaccharide unit, adjacent monosaccharide units being linked by 1→2, 1→3, 1→4 and/or 1→6 glycosidic bonds, and n is an integer of from 1 to 5, preferably 3 or 4.

As used herein, the term "anticoagulant and/or antithrombotic treatment" is intended to encompass both prophylactic and therapeutic treatment of a patient in need of such treatment.

DETAILED DESCRIPTION OF THE INVENTION

The sulfated oligosaccharides which are used in accordance with this invention are based on polymers of monosaccharide units, which may be linked by 1→2, 1→3, 1→4 and/or 1→6 glycosidic bonds and which may consist of from 3 to 8 monosaccharide units. Preferably, the oligosaccharides consist of from 3 to 6 monosaccharide units (that is n is from 1 to 4), more preferably from 5 to 6 monosaccharide units (n is from 3 to 4). The polymers may comprise homopolymers containing only one type of monosaccharide unit, or heteropolymers containing two or more different types of monosaccharide units, although homopolymers are preferred.

The monosaccharide units which are linked together to form the oligosaccharides are preferably hexoses, and may be either furanoses such as fructose or pyranoses such as glucose, mannose, altrose, allose, talose, galactose, idose, or gulose. Particularly preferred hexoses are glucose and mannose. The hexoses may be in either the D- or the L-configuration.

Each monosaccharide unit may be a hexose, hexuronic, hexosamine or N-acetylhexosamine.

The oligosaccharides of general formulae I and II also include compounds wherein the monosaccharide units are derivatised, in particular where the units are phosphate, acetyl or other ester derivatives of monosaccharides.

In general, the sulfated oligosaccharides of this invention may be prepared by sulfation of oligosaccharides by methods known per se in the art to give their corresponding O-sulfated derivatives. Suitable sulfation methods are described in International Patent Application No. PCT/AU96/00238, the contents of which are incorporated by reference. The oligosaccharides to be sulfated may be naturally occurring products including oligosaccharides prepared by enzymatic or chemical degradation of naturally occurring polysaccharides (such as amylose, dextran, cellulose, laminarin, pectin, chitin, chitosan, mannan, and a phosphomannan exopolysaccharide from the yeast *Pichia holstii*). Alternatively, the oligosaccharides may be prepared synthetically by the process disclosed in International Patent Application No. PCT/AU96/00238.

As previously described, sulfated oligosaecharides falling within the scope of this invention have been shown to exhibit anticoagulant and/or antithrombotic activity, and accordingly in yet another aspect the present invention extends to the use of a sulfated oligosaccharide as described above as an anti-anticoagulant and/or antithrombotic agent in the treatment of a warm-blooded animal (including a human) patient.

The invention also extends to the use in the manufacture of a medicament for the anticoadulant and/or antithrombotic treatment of a human or other warm-blooded animal patient of at least one sulfated oligosaccharide as described above.

Furthermore, this invention also provides a pharmaceutical or veterinary composition for anticoagulant and/or antithrombotic treatment, which comprises at least one sulfated oligosaccharide as described above, together with a pharmaceutically and veterinarily acceptable carrier or diluent therefor.

The active component is administered in therapeutically effective amounts, A therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

The formulation of therapeutic compositions is well known to persons skilled in this field. Suitable pharmaceutically or veterinarily acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically and veterinarily active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical and veterinary compositions of the present invention is contemplated Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human or animal subjects to be treated; each unit containing a predetermined quantity of active ingredient calculated to produce the desired therapeutic effect in association with the required pharmaceutical or veterinary carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

A variety of administration routes are available, although oral delivery is preferred because of the convenience to the patient. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, transdermal or parenteral (e.g. subcutaneous, intramuscular and intravenous) routes. Formulations for oral administration include discrete units such as capsules, tablets, lozenges and the like. Other routes include intrathecal administration directly into spinal fluid, direct introduction such as by various catheter and balloon angioplasty devices well known to those of ordinary skill in the art, and intraparenchymal injection into targeted areas.

Compositions of the present invention suitable for oral administration may be presented as discrete units such as capsules, cachets, tablets or lozenges, each containing a predetermined amount of the active component, in liposomes or as a solution or suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems n which the active component permeates at a controlled rate through a polymer. In addition, pump-based hardware delivery system can be used, some of which are adapted for implantation.

As previously described, in accordance with this invention the sulfated oligosaccharides may be used in treatment of many thrombotic and cardiovascular diseases, the most notable of these being deep venous thrombosis, pulmonary embolism, thrombotic stroke, peripheral arterial thrombosis, unstable angina and myocardial infarction.

Throughout this specification, unless the context requires otherwise, the word "comprise", or variations such as "comprises" or "comprising", will be understood to imply the inclusion of a stated integer or group of integers but not the exclusion of any other integer or group of integers.

Further features of the present invention are more fully described in the following Example(s). It is to be understood, however, that this detailed description is included solely for the purposes of exemplifying the present invention, and should not be understood in any way as a restriction on the broad description of the invention as set out above.

In the accompanying drawings:

FIG. 1 shows an analysis of the anticoagulant activity of a series of maltose based sulfated oligosaccharides of different chain length as measured by the activated partial thromboplastin time (APTT) test. Heparin (anticoagulant activity 120 U/mg) is included for comparison. Data obtained with pooled plasma from 90 donors, the coagulation time of the plasma being 30.8 seconds in the absence of inhibitors. Results representative of four separate experiments.

Figure 1:
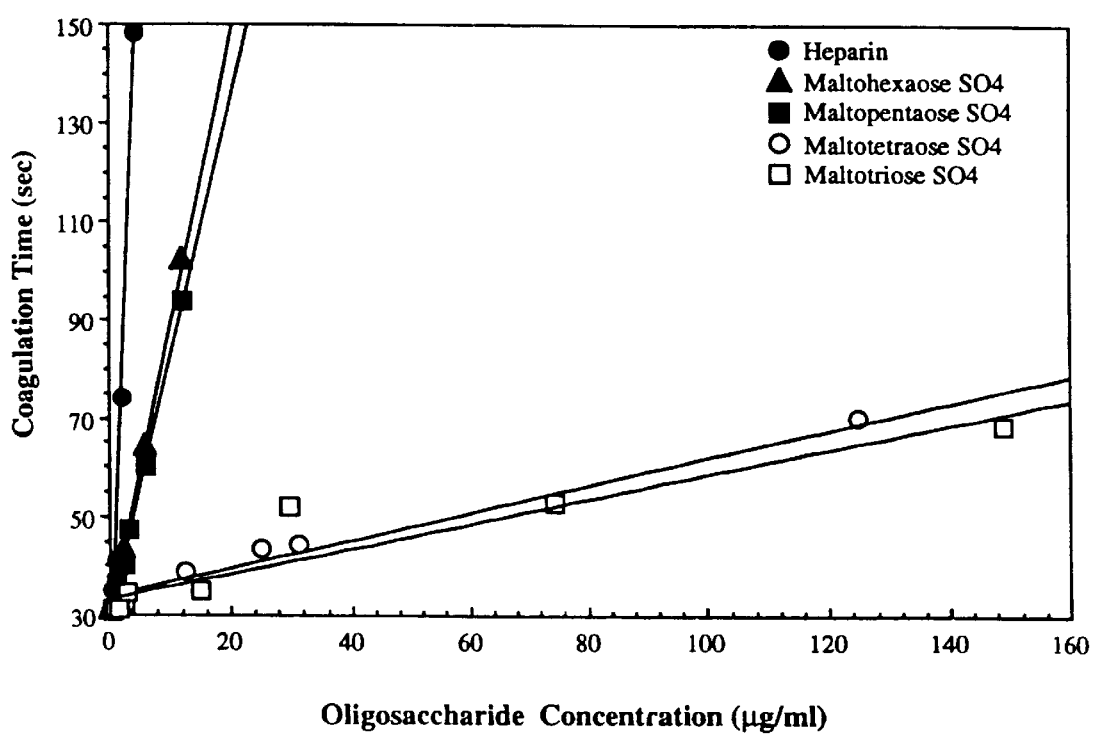

EXAMPLE 1
Preparation of Sulfated Oligosaccharides

In the present Examples, two sources of oligosaccharides were used for subsequent sulfation. The first source represents oligosaccharides derived from naturally occurring polysaccharides. The usual preparation procedure involves partial depolymerisation of the polysaccharides by enzymatic or chemical means and size fractionation of the resultant oligosaccharides. Examples of polysaccharides from which oligosaccharides were generated are amylose, dextran, cellulose, laminaran, pectin, chitin, chitosan, mannan and a phosphomannan exopolysaccharide from the yeast *Pichia holstii*. The second source represents totally synthetic hexose-containing oligosaccharides prepared by chemical polymerisation of hexose monomers. Prior International Patent Application No. PCT/AU96/00238 discloses a method for the manufacture of these totally synthetic oligosaccharides. The same patent application describes a procedure for the isolation of a mannopentaose phosphate of the structure P-6-Man-α-(1→3)-Man-α-(1→3)-Man-α-(1→3)-Man-α-(1→2)Man from the exopolysaccharide of the yeast *Pichia holstii*. The other naturally occurring oligosaccharides were purchased from Seikagaku, Tokyo, Japan. Finally, all of the oligosaccharides were sulfated by a procedure disclosed in Prior International Patent Application No. PCT/AU96/00238.

EXAMPLE 2
Anticoagulant Activity of the Sulfated Oligosaccharides

Table 1 summarises the anticoagulant activity of 19 sulfated oligosaccharides, as measured by the activated partial thromboplastin time (APTT) test. Similar results were obtained with the thrombin time test. At the outset it is clear that 11 of the sulfated oligosaccharides tested exhibit considerable anticoagulant activity when compared with heparin and Fragmin (LMW heparin). Chain length, monosaccharide makeup and linkage, all appear to be critical factors. The influence of chain length is particularly evident with the maltose series where the di-, tri- and tetrasaccharides exhibit low activity whereas the maltopentaose, maltohexaose and maltoheptaose sulfates are quite effective anticoagulants (Table 1, FIG. 1). Furthermore, a striking feature of the maltose series is that chain elongation y a single residue from the maltotetraose to maltopentaose results in a 19-fold increase in anticoagulant activity. The importance of monosaccharide composition is highlighted by chitosan hexamer sulfate, which is composed of β1-4 linked glucosamine, and exhibits negligible anticoagulant activity compared with β1-4 linked glucohexaose (cellohexaose, Table 1). The glucose series of oligosaccharides emphasizes the importance of monosaccharide linkage on activity. Thus, the sulfated laminarin series (β1-3 linked glucose) exhibits much lower anticoagulant activity than the sulfated α1-4, α1-6 and 1-4 linked glucose containing oligosaccharides (Table 1). There are additional, more subtle, effects of monosaccharide linkage on anticoagulant activity. Generally the penta- and hexasaccharide sulfates of either glucose or mannose linked α1-2, α1-3, α1-4 and α1-6 possess comparable anticoagulant activity (Table 1). The one exception is isomaltopentaose sulfate, which is a substantially less effective anticoagulant than the maltopentaose and mannopentaose sulfates (Table 1, FIG. 2). This suggests that anticoagulant activity is expressed by shorter chain α1-4 than α1-6 glucose polymers. Similarly, when glucose is β1-4 linked even shorter chain sulfated oligosaccharides are active, in this case the tetrasaccharide cellotetraose, being a reasonably potent anticoagulant (Table 1). Finally, two mannopentaose phosphate sulfates (PI-88's) with slightly different degrees of sulfation, were essentially equally active suggesting that providing sulfation of the oligosaccharides is >50% anticoagulant activity is assured.

Figure 2:
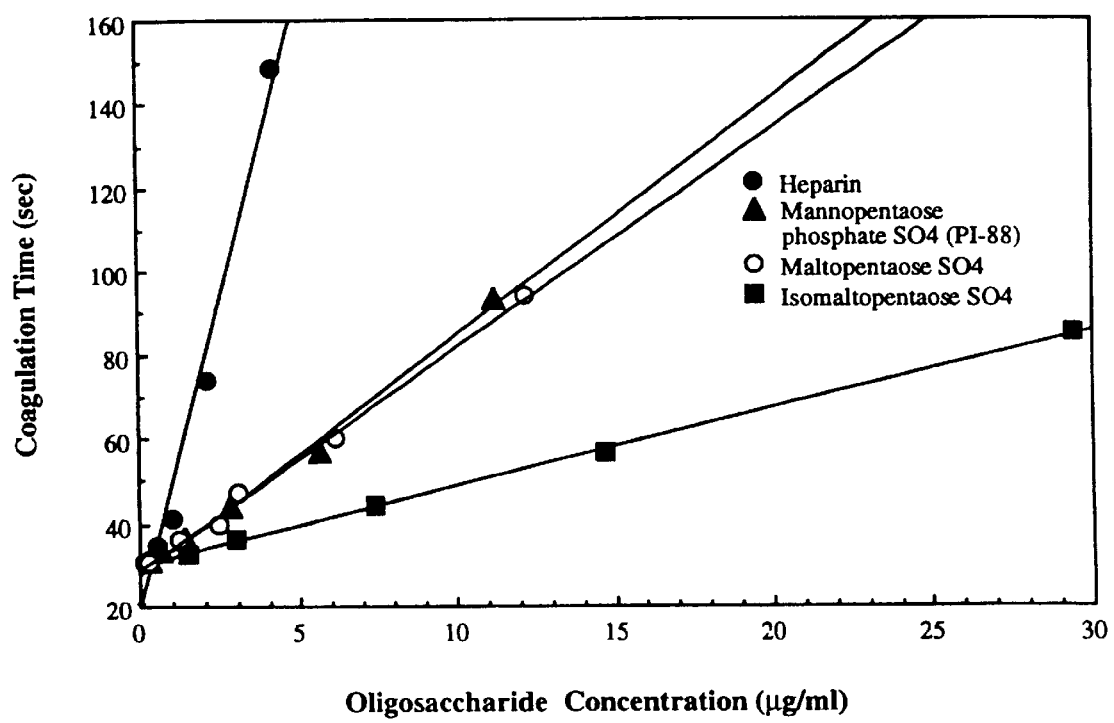
FIG. 2 shows a comparison of the anticoagulant activity of different sulfated pentasaccharides as measured by the APTT test, with heparin being included for comparison. Other details as in legend to FIG. 1.

Based on the data presented in Table 1 and FIGS. 1 and 2 it is clear that many of the active sulfated oligosaccharides display comparable anticoagulant activities, the slopes of the dose response curves of the seven most active being from 4.5 to 5.9-fold less steep than that of heparin. Thus, these oligosaccharide-based anticoagulants possess a much wider therapeutic window than heparin, a desirable feature if one wishes to tightly control the anticoagulation state of a patient.

Another feature of the sulfated oligosaccharide-based anticoagulants is that their dose response curves are extremely linear, with the correlation coefficients of the linear regression lines being >0.99 in most cases (Table 1).

Such an extreme linearity in responsiveness is not seen with heparin. This reproducibility in responsiveness was confirmed when the anticoagulant activity of mannopentaose phosphate sulfate (PI-88) was tested on plasma from 20 different donors. When plasma was anticoagulated to a similar extent by heparin and PI-88, overall the PI-88 gave a more reproducible prolongation of coagulation time, ie, 88.3±11.9 sec compared with 77.5±20.8 sec for heparin (Table 2). In fact, one donor (#13) failed to respond to heparin but responded, as expected, to PI-88 (Table 2).

Figure 3:
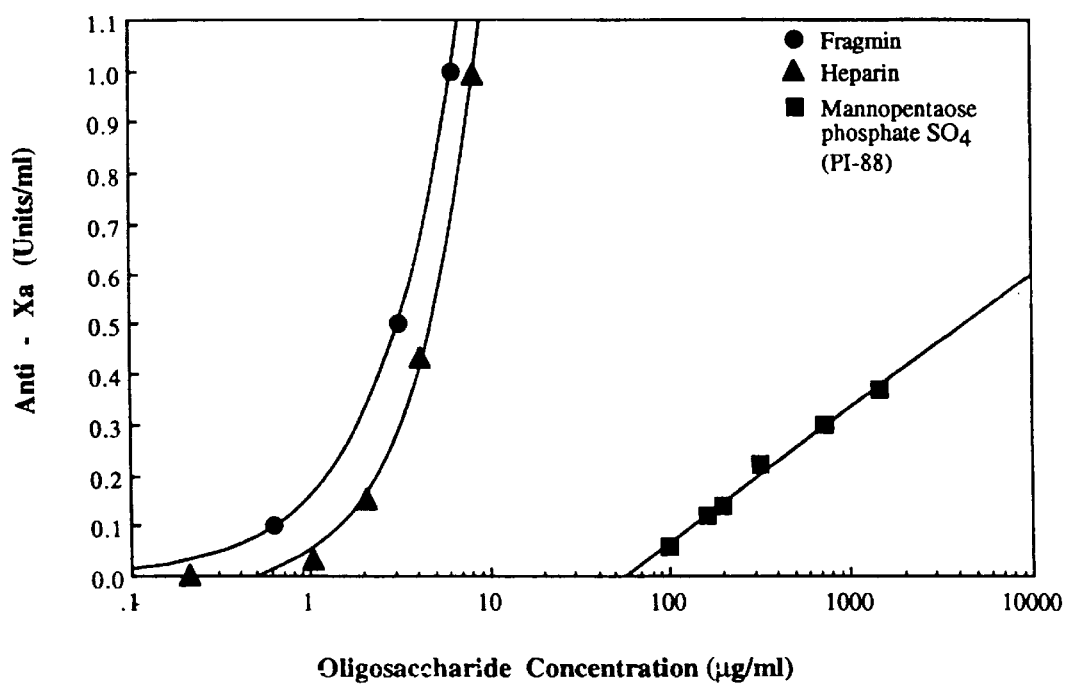
FIG. 3 shows a comparison of the anti-thrombin III mediated anti-factor Xa activity of heparin, LMW heparin (Fragmin) and the sulfated oligosaccharide mannopentaose phosphate sulfate (PI-88). Factor Xa activity was determined with the chromogenic (Helena) anti-Xa assay run on a Roche COBAS Fara biochemistry analyser.

The manner by which the sulfated oligosaccharides inhibit the coagulation cascade was then investigated. Initial studies showed that PI-88 did not enhance the ability of anti-thrombin III to inhibit thrombin. In fact, two different chromogenic assays revealed that PI-88 is 700–7000 fold less active than heparin in enhancing anti-thrombin III mediated anti-thrombin activity (data not shown). When examined for anti-thrombin III mediated factor Xa inhibitory activity it was found that PI-88 was at least 100–1000-fold less active than heparin or LMW heparin (Fragmin) (FIG. 3). These results imply that PI-88, and probably the other active sulfated oligosaccharides, do not exert their anticoagulant activity via antithrombin III. However, subsequent studies showed that the sulfated oligosaccharides with anticoagulant activity are probably acting via heparin cofactor II, thus resembling dermatan sulfate in their anticoagulant properties. In a plasma free system in which purified heparin cofactor II was added to thrombin and a chromogenic thrombin substrate, it was found that PI-88 enhanced the ability of heparin cofactor II to inhibit thrombin as effectively as heparin and dermatan sulfate (data not shown).

Collectively, these data indicate that sulfated oligosaccharide, like PI-88, resemble dermatan sulfate and therefore may have considerable potential as anti-thrombotic agents. Some additional biological properties of one of the sulfated oligosaccharides, PI-88, were defined. It was found to be a very weak inhibitor of collagen- and ADP-induced platelet aggregation (Table 3), further highlighting the specificity of action of sulfated oligosaccharides on the coagulation system. Protamine is frequently used clinically to reverse the anticoagulant effects of heparin and Fragmin. It was found that protamine also can effectively inactivate the anticoagulant activity of PI-88 (Table 4), indicating that protamine could be used as an effective in vivo antidote for sulfated oligosaccharides with anticoagulant properties. Finally, PI-88 was examined for its ability to act as an anticoagulant in a range of mammalian species. The compound was found to be an effective anticoagulant of human, marmoset, sheep, dog, rat and mouse plasma but was only weakly active in rabbit plasma (Table 5). Thus, sulfated oligosaccharides potentially can be used as anticoagulants/antithrombotics not only in humans but in a wide range of mammalian species.

TABLE 1

Comparison of the Anticoagulant Activity of Different Sulfated Oligosaccharides as Measured by the Activated Partial Thromboplastin Time (APTT) Test

| Compound | Monosaccharide Constituents | Linkage | Degree of Sulfation[a] | Increase in Coagulation Time (sec)/µg[b] | Correlation Coefficient[c] |
|---|---|---|---|---|---|
| Heparin | Glc, IdoA, GlcNAc | β1–4, α1–4 | ND | 29.69 | 0.977 |
| LMW Heparin (Fragmin) | Glc, IdoA, GlcNAc | β1–4, α1–4 | ND | 11.20 | 0.997 |
| Maltose SO4 | Glc | α1–4 | 6/8 (75%) | 0.31 | 0.995 |
| Maltotriose $SO_4$ | Glc | α1–4 | 9/11 (82%) | 0.25 | 0.892 |
| Maltoetraose $SO_4$ | Glc | α1–4 | 11/14 (79%) | 0.28 | 0.992 |
| Maltopentaose $SO_4$ | Glc | α1–4 | 9/17 (53%) | 5.25 | 0.996 |
| Maltohexaose $SO_4$ | Glc | α1–4 | 16.6/20 (83%) | 5.85 | 0.999 |
| Maltoheptaose $SO_4$ | Glc | α1–4 | ND | 5.9 | — |
| Isomaltopentaose $SO_4$ | Glc | α1–6 | 14/17 (82%) | 1.85 | 0.999 |
| Isomaltohexaose $SO_4$ | Glc | α1–6 | 12.8/20 (64%) | 6.56 | 0.999 |
| Cellotetraose $SO_4$ | Glc | β1–4 | ND | 4.2 | — |
| Cellopentaose $SO_4$ | Glc | β1–4 | ND | 3.5 | — |
| Cellohexaose $SO_4$ | Glc | β1–4 | ND | 4.8 | — |
| Laminaritetraose $SO_4$ | Glc | β1–3 | ND | 2.9 | — |
| Laminarihexaose $SO_4$ | Glc | β1–3 | ND | 0.9 | — |
| Laminariheptaose $SO_4$ | Glc | β1–3 | ND | 0.5 | — |
| Chitosan hexamer $SO_4$ | GlcN | β1–4 | ND | 0.4 | — |
| Mannopentaose $SO_4$[d] | Man | α1–3, α1–6 | 11/17 (65%) | 5.32 | 0.985 |
| Mannopentaose phosphate $SO_2$ (PI-88)[e] | Man | α1–3, α1–2 | 12.5/16 (78%) | 5.67 | 0.995 |
| Mannopentaose phosphate $SO_4$ (PI-88)[e] | Man | α1–3, α1–2 | 14/16 (88%) | 5.04 | 0.995 |
| Sucrose $SO_4$ | Glc, Frc | α1–2 | 8/8 (100%) | 0.39 | 0.994 |

[a]Actual number of sulfate groups attached/theoretical maximum number of sulfate groups which can be coupled to each molecule. Values in brackets represents % sulfation. In cases where degree of sulfation not determined (ND) oligosaccharides sulfated under conditions which would result in maximum sulfation.
[b]Data expressed as increase in coagulation time (seconds) resulting from a 1 µg/ml increase in concentration of the test compound. Values obtained from a linear regression analysis of the coagulation data.
[c]Correlation coefficient obtained following linear regression analysis of the coagulation data. When no value given insufficient data points for a correlation coefficient to be calculated.
[d]Totally synthetic mannopentaose.
[e]Mannopentaose phosphate isolated from the yeast *Pichia holstii* which contains mannose-6-phosphate at the reducing terminus.
ND = not determined

TABLE 2

Assessment of Donor Variability in the Anticoagulant Activity of Heparin and Mannopentaose Phosphate SO$_4$ (PI-88)

| | Coagulation Time (sec)[a] | | |
|---|---|---|---|
| Normal Donor | Control (2.1 μg/ml) | Heparin phosphate SO$_4$ *PU-88) (8.6 μg/ml) | Mannopentaose |
| 1 | 30.5 | 72.8 | 77.3 |
| 2 | 34.8 | 93.7 | 89.6 |
| 3 | 31.6 | 95.4 | 94.0 |
| 4 | 31.3 | 78.1 | 85.6 |
| 5 | 33.4 | 110.5 | 101.9 |
| 6 | 31.3 | 78.2 | 95.0 |
| 7 | 38.9 | 110.6 | 115.3 |
| 8 | 34.9 | 101.6 | 101.9 |
| 9 | 31.5 | 70.1 | 85.2 |
| 10 | 30.5 | 72.7 | 78.0 |
| 11 | 34.9 | 89.5 | 93.6 |
| 12 | 33.1 | 73.8 | 82.9 |
| 13 | 35.8 | 40.1 | 85.5 |
| 14 | 31.1 | 85.6 | 89.7 |
| 15 | 34.6 | 69.7 | 81.2 |
| 16 | 27.9 | 64.1 | 72.6 |
| 17 | 34.8 | 101.9 | 108.0 |
| 18 | 27.3 | 48.7 | 70.4 |
| 19 | 35.4 | 73.4 | 93.6 |
| 20 | 30.6 | 57.0 | 72.6 |
| Mean ± SD | 32.8 ± 2.8 | 77.5 ± 20.8 | 88.3 ± 11.9 |

[a]Coagulation times estimated using the APTT test. Similar results were obtained in duplicate assays. Concentrations of heparin and mannopentaose phosphate SO$_4$ (PI-88) were used which prolonged the coagulation time by approximately 2.5 fold. Donor 13 highlighted in bold italics as this donor failed to respond to heparin but responded to mannopentaose phosphate SO$_4$.

TABLE 3

Inhibition of Platelet Aggregation by Mannopentaose Phosphate SO$_4$ (PI-88)

| | Relative Rate of Platelet Aggregation[a] | |
|---|---|---|
| PI-88 Concentration (μg/ml) | Collagen-induced Aggregation | ADP-induced Aggregation |
| 0 | 114 ± 8 | 81 ± 1 |
| 21 | 97 ± 8 | 74 ± 1 |
| 210 | 86 ± 10 | 72 ± 1 |
| 2100 | 79 ± 0 | 56 ± 2 |

[a]Human platelet aggregation induced by either collagen (9 μg/ml) or ADP (10 μM) and relative rates of platelet aggregation estimated, in the presence or absence of PI-88, using a platelet aggregometer. Data ± SD representative of two platelet donors.

TABLE 4

Reversal of Anticoagulant Activity of Heparin, Fragmin and PI-88 by Protamine Sulfate

| Anticoagulant | Protamine Sulfate Concentration | Coagulation Time (seconds)[a] |
|---|---|---|
| Nil | — | 31.6 |
| Nil | 10 μg/ml | 34.4 |
| Heparin (2.1 μg/ml) | — | 91.9 |
| Heparin (2.1 μg/ml) | 10 μg/ml | 33.4 |
| Fragmin (6.25 μg/ml) | — | 109.0 |
| Fragmin (6.25 μg/ml) | 10 μg/ml | 38.0 |

TABLE 4-continued

Reversal of Anticoagulant Activity of Heparin, Fragmin and PI-88 by Protamine Sulfate

| Anticoagulant | Protamine Sulfate Concentration | Coagulation Time (seconds)[a] |
|---|---|---|
| PI-88 (8.6 μg/ml) | — | 79.7 |
| PI-88 (8.6 μg/ml) | 10 μg/ml | 43.6 |

[a]Coagulation times estimated by the APTT test.
PI-88 = sulfated mannopentaose phosphate from *Pichia holstii*.

TABLE 5

Anticoagulant Activity of Heparin, Fragmin and PI-88 with Plasma from Different Mammalian Species

| | Relative Increase in Coagulation Time[a] | | | |
|---|---|---|---|---|
| Species | Heparin (0.83 μg/ml) | Fragmin (6.25 μg/ml) | PI-88 (2.24 μg/ml) | PI-88 (22.4 μg/ml) |
| Human | 1.31 | 3.02 | 1.42 | 4.65 |
| Marmoset | 1.26 | 2.71 | 1.40 | 2.86 |
| Sheep | 1.10 | 1.42 | 1.88 | >4.98 |
| Rabbit | 1.25 | 1.85 | 1.02 | 1.20 |
| Dog | 1.01 | 1.32 | 1.24 | 2.42 |
| Rat | 1.02 | 1.90 | 1.54 | >5.88 |
| Mouse | ND | ND | 1.13 | 3.03 |

[a]Coagulation times estimated by the APTT test. Data expressed as fold increase in coagulation time induced by the anticoagulant compared with untreated control.
PI-88 = sulfated mannopentaose phosphate from *Pichia holstii*.
ND = not determined.

References

1. Björk, I. and Lindahl, U. (1982) *Mot. Cell Biochem.* 48, 161–182.
2. Björk, I., Olson, S. T. and Shane, J. D. (1989). In "Heparin: Chemical and Biological Properties, Clinical Applications" (Lane, D. L. and Lindahl, U., eds) pp 229–255, Edward Arnold Ltd., London.
3. Olsen, S. T. and Björk, I. (1994). Regulation of thrombin activity by antithrombin and heparin. *Sem. Thromb. Hem.* 20, 373409.
4. Lindahl, U. (1989). In "Heparin" (Lane, D. A. and Lindahl, U., eds) pp. 159–189, CRC Press.
5. Hirsch, J. and Levine, M. N. (1992) Low-molecular-weight heparin. *Blood* 79, 1–17.
6. Beijering, R. J. R., ten Cate, H. and ten Cate, J. W. (1996). *Ann. Hematol.* 72, 177–183.
7. Agnelli, G., Cosmi, B., Di Filippo, P. et al. (1992). *Thromb. Haemost.* 67, 203–208.
8. Bourin, M. -C. and Lindahl, U. (1993). *Biochem. J.* 289, 313–330.

What is claimed is:

1. A method for the anticoagulant and/or antithrombotic treatment of a human or other warm-blooded animal patient in need of such treatment, which comprises administration to the patient of an effective amount of at least one sulfated oligosaccharide, wherein the oligosaccharide has the general formula I:

$$R_1-(R_x)_n-R_2 \qquad (I)$$

wherein $R_1$ and $R_2$ and each $R_x$ represents a hexose monosaccharide unit, all of which may be the same or different, adjacent monosaccharide units being linked by 1→2, 1→3, 1→4 and/or 1→6 glycosidic bonds and n is an integer of from 1 to 6.

2. A method according to claim 1 wherein in the oligosaccharide of general formula I n is 3 or 4.

3. A method according to claim 1 or claim 2, wherein in the oligosaccharide of general formula I, the monosaccharide units are selected from the group consisting of fructose, glucose, mannose, altrose, allose, talose, galactose, idose and gulose.

4. A method according to claim 1, wherein the oligosaccharide has the general formula II:

$$R\text{---}(R)_{n-R} \tag{II}$$

wherein each R group is the same and each represents a hexose monosaccharide unit, adjacent monosaccharide units being linked by 1→2, 1→3, 1→4 and/or 1→6 glycosidic bonds; and n is an integer of from 1 to 5.

5. A method according to claim 4, wherein in the oligosaccharide of general formula II, n is from 3 or 4.

6. A method according to claim 4 or claim 5, wherein in the oligosaccharide of general formula II, R represents a monosaccharide unit which is selected from the group consisting of glucose, mannose, altrose, allose, talose, galactose, idose and gulose.

7. A method according to claim 6, wherein in the oligosaccharide of general formula II, R represents glucose or mannose.

8. A method according to claim 1, wherein the oligosaccharide is prepared by enzymatic or chemical degradation of a naturally occurring polysaccharide.

9. A method according to claim 8, wherein the oligosaccharide is an amylose-, dextran-, cellulose-, laminarin-, or mannan-oligosaccharide.

10. A method according to claim 9, wherein the oligosaccharide is selected from maltopentaose, malothexaose, maltoheptaose, isomaltopentaose, isomaltohexaose, cellotetraose, cellopentaose, cellohexaose, laminaritetraose and mannopentaose.

11. A method according to claim 8, wherein the oligosaccharide is mannopentaose phosphate from the yeast *Pichia holstii*.

12. A method according to any of claims 1, 2, 4, 5, or 8–11, wherein the treatment comprises treatment of a thrombotic or cardiovascular disease.

13. A method according to claim 12, wherein the treatment comprises treatment of deep-vein thrombosis, pulmonary embolism, thrombotic stroke, peripheral arterial thrombosis, unstable angina or myocardial infarction.

14. A method according to claim 3, wherein the treatment comprises treatment of a thrombotic or cardiovascular disease.

15. A method according to claim 6, wherein the treatment comprises treatment of a thrombotic or cardiovascular disease.

16. A method according to claim 14, wherein the treatment comprises treatment of deep-vein thrombosis, pulmonary embolism, thrombotic stroke, peripheral arterial thrombosis, unstable angina or myocardial infarction.

17. A method according to claim 15, wherein the treatment comprises treatment of deep-vein thrombosis, pulmonary embolism, thrombotic stroke, peripheral arterial thrombosis, unstable angina or myocardial infarction.

18. A method according to claim 7, wherein the treatment comprises treatment of a thrombotic or cardiovascular disease.

19. A method according to claim 18, wherein the treatment comprises treatment of deep-vein thrombosis, pulmonary embolism, thrombotic stroke, peripheral arterial thrombosis, unstable angina or myocardial infarction.

* * * * *

UNITED STATES PATENT AND TRADEMARK OFFICE
CERTIFICATE OF CORRECTION

PATENT NO.   : 6,271,215 B1
DATED        : August 7, 2001
INVENTOR(S)  : Christopher Richard Parish, William Butler Cowden Page 1 of 1

It is certified that error appears in the above-identified patent and that said Letters Patent is hereby corrected as shown below:

Columns 7 & 8,
Table 1, under "Compounds", 3rd from last entry, change "$SO_2$", to read -- $SO_4$ --.

Column 11, claim 4,
Line 11, change equation "$R\text{-}(R)_{n\text{-}R}$", to read -- $R\text{-}(R)_n\text{-}R$ --.

Signed and Sealed this

Fifth Day of March, 2002

Attest:

Attesting Officer

JAMES E. ROGAN
Director of the United States Patent and Trademark Office